United States Patent [19]

Ridgeway

[11] 3,974,567
[45] Aug. 17, 1976

[54] TEMPORARY DENTAL CROWN PROTECTOR

[76] Inventor: William V. Ridgeway, 265 Redondo Ave., Long Beach, Calif. 90803

[22] Filed: Apr. 24, 1975

[21] Appl. No.: 571,256

[52] U.S. Cl. .......................................... 32/1; 32/15
[51] Int. Cl.² .......................................... A61C 19/00
[58] Field of Search ................. 32/1, 21, 15, 16, 12; 40/2 R; 206/813, 409

[56] References Cited
UNITED STATES PATENTS 2,170,147   8/1939   Lane ..................................... 40/2 R

FOREIGN PATENTS OR APPLICATIONS 1,227,100   8/1960   France ............................. 40/2 R
1,322,187   2/1963   France .............................. 206/409

OTHER PUBLICATIONS

"Datamark Stock Labels," Datamark Inc., Cleveland, Ohio, Received 11/1967.

*Primary Examiner*—Jack Q. Lever
*Attorney, Agent, or Firm*—William C. Babcock

[57] ABSTRACT

A temporary protector defined by a sheet of pliable paper or like material of such shape and size as to cover the masticating or occlusal surface of a dental crown. The sheet has first and second sides, with the first side being covered with a film of pressure sensitive adhesive. The film of pressure sensitive adhesive on each protector permits the latter to be removably bonded to the masticating surface of a dental crown prior to the crown being permanently secured to a prepared tooth by the use of conventional means, I.E. a crown and bridge cement, polycarboxylate cement, or the like. Each protector prevents the undulating masticating surface of the dental crown on which it is mounted from being contaminated with cement during the time it is being mounted on the prepared tooth structure. Removal of tiny particles of solidified cement from the surface of a dental crown after it is positioned on a tooth is a tedius, time-consuming operation and one that is completely avoided by use of the protector abovedescribed. The protectors prior to being used are preferably lightly bonded in longitudinal sequence on a first surface of a strip of pliable sheet material such as paper or the like, which strip is wound in the form of a roll and rotatably disposed in the interior of a transversely slotted housing.

3 Claims, 7 Drawing Figures

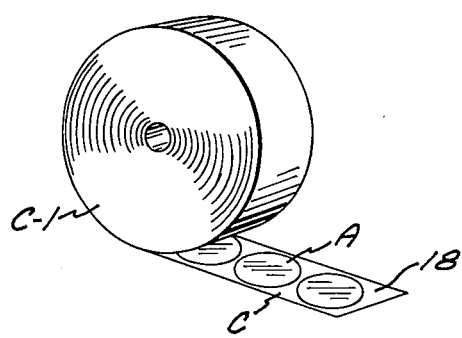
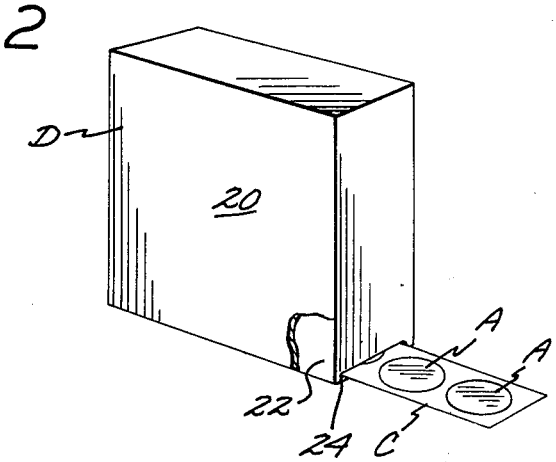
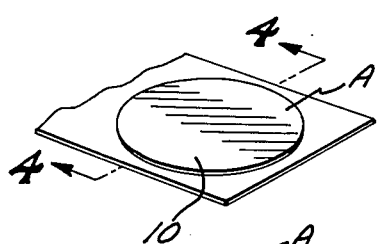
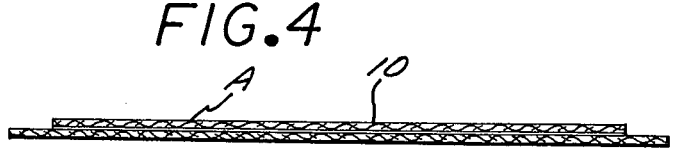
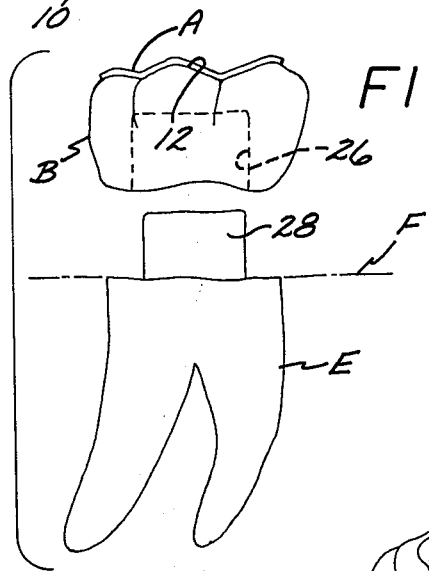
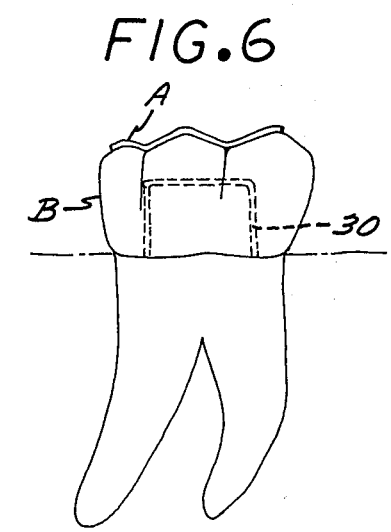
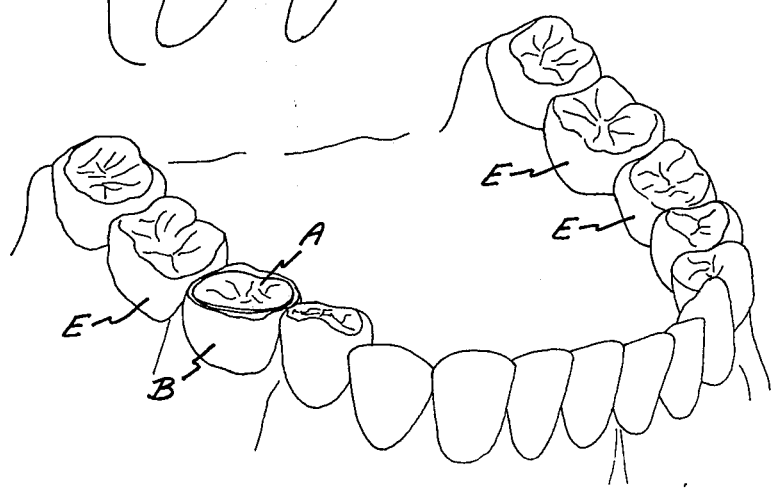

TEMPORARY DENTAL CROWN PROTECTOR

BACKGROUND OF THE INVENTION

1. Field of the Invention

A temporary dental crown protector.

2. Description of the Prior Art

In dentistry, it is common practice for various reasons to partially remove an exposed portion of a molar, or bicuspid, and the portion of the molar or bicuspid remaining being thereafter enveloped and permanently engaged by a recessed crown that has substantially the same external configuration as the original molar or bicuspid. The crown is permanently bonded to the remaining portion of the molar by a dental crown and bridge cement.

During the positioning of the crown on the remaining portion of the molar by a dentist, tiny particles of the cement may inadvertently contact and adhere to the masticating surface of the dental crown is tedious and time-consuming for the dentist.

The major object of the present invention is to provide a temporary protector that is easily and quickly mounted on the masticating surface of a dental crown to prevent particles of crown and bridge cement adhering to the surface when the crown is permanently mounted on a molar or bicuspid.

Another object of the invention is to supply the protectors in an easily usable form of variable sizes in which they are lightly bonded to a sheet of paper or like material that serve as a carrier or support therefor, and from which the protectors may be sequentially removed by a dentist as required to be disposed in a temporary postion on the masticating surface of a dental crown.

SUMMARY OF THE INVENTION

Each temporary dental crown protector is defined by a first sheet of pliable paper or like material of such shape and area as to cover the masticating surface of a crown. The sheet has first and second sides, with the first side being covered by a film of pressure sensitive adhesive. The film of pressure sensitive adhesive on each protector permits the latter to be removably bonded to the masticating surface of a dental crown prior to the latter being permanently secured to a prepared molar by use of a crown and bridge cement or like material.

The protectors, prior to being used for their intended purpose, are preferably lightly bonded in longitudinally spaced relationship on a first surface of a strip of pliable sheet material such as paper, which strip is wound in the form of a roll that is rotatably disposed in the interior of a transversely slotted housing. When a protector is needed, the dentist withdraws an end segment of the strip through the slot in the housing, and removes a protector therefrom by the use of a suitable instrument. The removed protector is then temporarily mounted on the masticating surfaces of a dental crown by pressing the film of pressure sensitive adhesive on the protector into contact with the portion of the crown that is to be protected. The housing serves to maintain the protectors that are bonded to the strip within the interior thereof in a sanitary condition until needed.

BRIEF DESCRIPTION OF THE DRAWING

FIG. 1 is a perspective view of an elongate strip of pliable material such as paper, that has a number of the temporary crown protectors adhered thereto;

FIG. 2 is a perspective view of a slotted housing that rotatably supports the roll of strip material shown in FIG. 1 in such a manner that the protectors may be sequentially removed from an end portion of the strip.

FIG. 3 is a perspective view of a portion of the strip shown in FIG. 1, and one of the temporary protectors removably supported thereon;

FIG. 4 is a transverse cross-sectional view of the strip and temporary protector shown in FIG. 3 taken on the line 4-4 thereof;

FIG. 5 is a side-elevational view of a molar that has the upper portion thereof ground to receive a dental crown and a dental crown having one of the temporary protectors mounted on the masticating surface thereof;

FIG. 6 is the same view as shown in FIG. 5, but after the dental crown has been secured to the molar by a crown and bridge cement; and FIG. 7 is a perspective view of the lower teeth of a patient, and illustrating one of the temporary protectors in temporary adhering contact with the masticating surface of a molar.

DESCRIPTION OF THE PREFERRED EMBODIMENT

Each of the temporary dental crown protectors A as best seen in FIGS. 3 and 4 is defined by a sheet 10 of a pliable material such as paper or the like that is preferably of a generally circular shape and of sufficient area as to cover the undulating masticating surface 12 of a dental crown B. The protectors A each have a first side 14 that is covered by a film 16 of a pressure sensitive adhesive.

The temporary protectors A as may be seen in FIG. 1 are lightly adhered by film 16 to a first side 18 of an elongate strip C, which strip is formed from a pliable sheet material such as paper. Film 16 serves a two-fold purpose; first, to removably adhere the crown protectors A to the first side 18 of strip C; and second, to temporarily bond the protectors to the masticating surfaces 12 of dental crowns B. The masticating surface 12 of the dental crown B is undulating in configuration, and the sheet 10 that defines the protector A must be sufficiently pliable as to conform thereto.

The strip C as may be seen is helix wound into the form of a roll C-1, and acts as a support or carrier for the protectors A prior to the latter being used. A housing D is provided as shown in FIG. 2 that is defined by two halves 20 and 22 that slidably engage one another as shown in FIG. 2. The housing halves 20 and 22 cooperate to define a confined space in the interior thereof in which the roll C-1 is disposed, with an end segment of the strip C projecting outwardly through a transverse slot 24 formed in the housing.

The crown B has a recess 26 extending upwardly therein, and this recess engaging an upper porton 28 of a molar E that has been reduced in size by a grinding operation by a dentist. Portion 28 is situated above the gum line F. The crown B is permanently secured to the molar portion 28 by the dentist interposing an amalgam cement 30 in the space defined between molar portion 28 and the wall portion of crown B that defines the recess 26. The crown B as may be seen in FIG. 5 has the protector A temporarily bonded thereto, and the protector remaining in place on the crown until it is permanently cemented to the molar portion 28 as shown in FIG. 6.

In FIG. 7 a crown B is shown in a permanently bonded position on a molar E, and with the protector A in a protecting position on the molar. After the crown B is permanently secured to a molar E by use of amalgam cement 30, the protector A is removed from the crown and discarded.

From the above description, it will be seen that the pressure sensitive adhesive film 16 serves both to removably hold the protectors A on the sheet 10 until needed, and when needed on the masticating surfaces 12 of crowns B.

The use and operation of the invention has been described previously in detail and need not be repeated.

I claim:

1. In combination with a support that has a surface of substantial area, a plurality of dental crown protectors mounted in spaced relationship on said first surface, each of said crown protectors including:

a. A sheet of material of sufficient area and of such shape as to cover the undulating masticating surface of said crown, with said sheet being sufficiently pliable as to conform to the configuration of said surface, and said sheet including a first side; and
   b. A film of pressure sensitive adhesive that covers the entire surface of said first side, said film serving the dual function of removably securing said crown protector to said first surface until said protector is needed, and said film serving to removably secure said sheet to said masticating surface of said crown to protect said masticating surface from contamination with a bonding agent during the mounting of said crown on a tooth.

2. The combination as defined in claim 1 in which said surface is defined by an elongate strip, and said protectors are removably adhered to said surface in longitudinally spaced relationship.

3. The combination as defined in claim 2 in which said strip is defined by a sheet material sufficiently pliable as to be formed into a roll.

* * * * *